US006579532B1

(12) United States Patent
Mandel et al.

(10) Patent No.: US 6,579,532 B1
(45) Date of Patent: Jun. 17, 2003

(54) ORTHOPEDIC MIXTURES PREPARED BY SUPERCRITICAL FLUID PROCESSING TECHNIQUES

(75) Inventors: Frederick S. Mandel, Chagrin Falls, OH (US); J. Don Wang, Brecksville, OH (US); Steven M. Howdle, Nottingham (GB); Vladimir K. Popov, Moscow (RU)

(73) Assignee: Ferro Corporation, Cleveland, OH (US)

(*) Notice: Subject to any disclaimer, the term of this patent is extended or adjusted under 35 U.S.C. 154(b) by 0 days.

(21) Appl. No.: 09/658,252

(22) Filed: Sep. 8, 2000

(51) Int. Cl.[7] ............................ A61F 2/28; A61K 31/74
(52) U.S. Cl. .................. 424/423; 424/78.17; 623/16.11
(58) Field of Search ............................ 424/423, 78.17; 623/16.11

(56) References Cited

U.S. PATENT DOCUMENTS

| 5,082,803 A | | 1/1992 | Sumita |
| 5,399,597 A | | 3/1995 | Mandel et al. |
| 5,424,076 A | * | 6/1995 | Gorissen et al. ............ 424/301 |
| 5,548,004 A | | 8/1996 | Mandel et al. |
| 5,698,163 A | | 12/1997 | Mandel |
| 5,989,289 A | | 11/1999 | Coates et al. |
| 5,993,747 A | | 11/1999 | Mandel |
| 6,005,162 A | | 12/1999 | Constantz |
| 6,054,103 A | | 5/2000 | Mandel |
| 6,174,934 B1 | * | 1/2001 | Sun et al. ................... 523/114 |

FOREIGN PATENT DOCUMENTS

| WO | 97/31691 | * | 9/1997 |
| WO | WO98/51347 | | 11/1998 |

OTHER PUBLICATIONS

Supercritical Fluids Eds. Kiran & Sengers pps. 541–565, Jul. 1993.*
ACS Symposium Series San Francisco Nov. 1994 pps. 258–280.*
THAR Bulletin 2000.*
U.S. patent application Ser. No. 09/315,616, Mandel, filed May 20, 1999.
F. Mandel, Manufacturing of Specialty Materials in Supercritical Fluid Carbon Dioxide, Inorganica Chimica Acta 294 (1999) 214–223.
K. Uhrich, Polymeric Systems for Controlled Drug Release, Journal of the American Chemical Society (1999).

* cited by examiner

Primary Examiner—Carlos Azpuru
(74) Attorney, Agent, or Firm—Rankin, Hill, Porter & Clark LLP

(57) ABSTRACT

Orthopedic mixtures are prepared by mixing starting materials and a process medium in a reactor to form a supercritical fluid slurry. The starting materials include a source of calcium ions and a polymer matrix for the calcium ions. The process medium preferably is carbon dioxide which is supplied to the reactor in a supercritical state or which is heated and pressurized in the reactor to attain a supercritical state. After mixing for a period of time, the slurry either is left in the reactor or is discharged into a receiving vessel. The process medium is separated from the other materials and removed, leaving behind a finely divided product. The finely divided product can be poured into a mold and cured. Thereafter, the cured product can be used as a bone implant or a bone implant can be carved from the cured product. Alternatively, if an ultraviolet light-curable catalyst and a monomer are included in the mixture, the finely divided product can be used as bone filler and cured in situ. After curing, the mixture produces a dense, strong, porous product that simulates autogenic bone.

29 Claims, 1 Drawing Sheet

ORTHOPEDIC MIXTURES PREPARED BY SUPERCRITICAL FLUID PROCESSING TECHNIQUES

BACKGROUND OF THE INVENTION

1. Field of the Invention.

The invention relates to the use of supercritical fluid processing techniques to prepare orthopedic mixtures. The mixtures can be used to make bone replacement implants or bone filler.

2. Description of the Prior Art.

There is a need for orthopedic parts such as bone implants. For example, in the to field of spinal surgery, removal of all or a portion of a damaged intervertebral disc requires that the resulting space be filled to prevent disc space collapse and to promote fusion of the adjacent vertebrae across the disc space. Desirably, the space will be filled with an implant that will have adequate strength to withstand loads imposed by the vertebrae and which will permit bone ingrowth. Although implants made of a metal such as titanium alloy have adequate strength, they have various drawbacks such as a tendency to have relatively long fusion times. Implants made of bone grafts are desirable because bone grafts are biological materials which are replaced over time with the patient's own bone, via the process of creeping substitution. Over time a bone graft virtually disappears, unlike a metal implant which persists indefinitely.

Unfortunately, bone grafts present several disadvantages. Autogenic bone is available only in limited quantities. The additional surgery also increases the risk of infection and blood loss and may reduce structural integrity at the donor site. The graft harvesting surgery is alleged to cause extreme pain that may exceed the pain of the fusion surgery. Allogenic and xenogenic bone grafts are undesirable because they involve the implantation of a bone of foreign origin into the body, with attendant risks of infection or rejection. Although bone graft substitutes are known, as exemplified by U.S. Pat. No. 5,082,803, they have various drawbacks such as the need to cure them by the use of high temperature, high pressure steam. Desirably, a bone substitute would be available that would have the advantages of autogenic bone (such as strength and bio-compatibility) and which would be easy to manufacture and use.

In addition to the need for pre-formed bone substitutes, there is a need for high quality bone filler. In certain circumstances a bone filler can be used to repair fissures, cracks, gaps, or other defects in existing bone. Also, a bone filler can be useful in correcting certain types of bone loss that are not amenable to the use of pre-formed bone implants or for which it is difficult or impossible to create a properly shaped bone implant. Further, in the particular case of surgical procedures such as total knee or hip replacement, a bone filler is necessary to cement the implanted prosthesis into the remaining bone structure. Although bone fillers are known, as exemplified by U.S. Pat. No. 6,005,162, there remains a need for a bone filler that is easy to use, which cures quickly in place without the production of excessive heat, and which produces a strong, secure filling.

SUMMARY OF THE INVENTION

In response to the foregoing concerns, the present invention provides a technique for the manufacture of orthopedic parts such as bone implants that have the desirable characteristics of autogenic bone, but without the drawbacks of allogenic bone, xenogenic bone, or existing bone substitutes. In addition, the present invention provides for the manufacture of a bone filler having superior characteristics.

Orthopedic mixtures according to the invention are prepared by charging a reactor with starting materials that will produce an orthopedic implant or filler of desired strength characteristics. The starting materials include a source of calcium ions and a polymer or multiple polymers that forms a matrix for the calcium source. A process medium is added to the reactor. The process medium preferably is carbon dioxide which is supplied to the reactor in a supercritical state or which is heated and pressurized in the reactor to attain a supercritical state. The heated and pressurized ingredients are mixed in the reactor for a period of time sufficient to form them into a homogeneous, gas-saturated suspension, or supercritical fluid slurry. After the ingredients have been mixed adequately, the slurry either is left in the reactor or is discharged into a receiving vessel where the process medium is separated from the remainder of the materials and removed, leaving a finely divided product behind.

The finely divided product can be poured into a mold and cured by heating the mold to a relatively low temperature. Thereafter, the cured product can be used as a bone implant or a bone implant can be carved from the cured product.

In those cases where the product is to be used as a bone filler, one of the starting materials is an ultraviolet light-curable catalyst. The finely divided product can be poured or injected directly into a fissure or other gap in a patient's bone and cured in situ by the application of ultraviolet light.

All of the orthopedic mixtures according to the invention produce a cured product that is dense, strong and porous, and which simulates autogenic bone. Typically, the cured product will have a high percentage of calcium, will be porous with 100% interconnectivity of pores (i.e., without isolated pores), and will have pore sizes on the order of 300–400 microns.

DESCRIPTION OF THE PREFERRED EMBODIMENT

Figure 1:
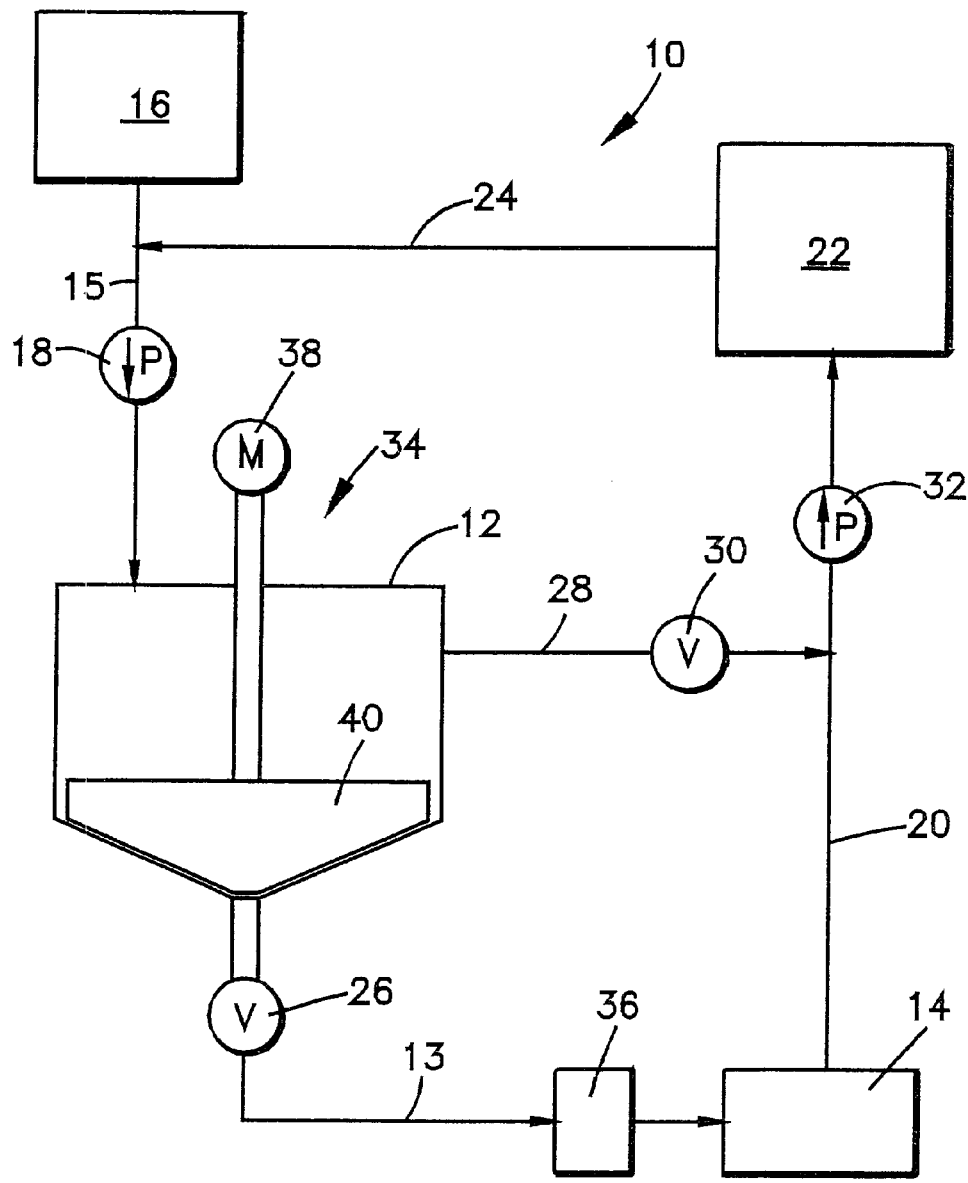
FIG. 1 is a schematic view of apparatus suitable for practicing the present invention.

Referring now to FIG. 1, apparatus for practicing the present invention is indicated generally by the reference numeral 10. The apparatus 10 is described in U.S. Pat. No. 5,399,597, entitled Method of Preparing Coating Materials, issued Mar. 21, 1995 to Frederick S. Mandel, et al. Reference also is made to U.S. Pat. No. 5,698,163, entitled Control System for Processes Using Supercritical Fluids, issued Dec. 16, 1997 to Frederick S. Mandel, for a description of a control system for the apparatus 10. Additional details of the apparatus 10 can be found in U.S. Pat. No. 6,054,103, entitled Mixing System for Processes Using Supercritical Fluids, issued to Frederick S. Mandel; U.S. application Ser. No. 09/315,616, entitled Delivery System for Processes Using Supercritical Fluids, filed May 20, 1999 by Frederick S. Mandel; and U.S. Pat. No. 5,993,747, entitled Mixing System for Processes Using Supercritical Fluids, issued Nov. 30, 1999 to Frederick S. Mandel. The disclosures of all of the patents and applications referred to in this paragraph are incorporated in the present specification by reference.

Continuing to refer to FIG. 1, the apparatus 10 includes a reactor 12 that is connected by conduit 13 to a receiving vessel 14. A conduit 15 connects the reactor 12 to a source 16 of a process medium such as liquid carbon dioxide. The process medium preferably is fed under pressure into reactor 12 using a compressor or liquid pump 18. The receiving vessel 14 is connected by conduit 20 to a return tank 22. The return tank 22 is connected by conduit 24 to the source 16 of the process medium.

Reactor 12 includes, preferably at its base, a valve 26 for facilitating the emptying of the contents of the reactor 12 into the receiving vessel 14. A conduit 28 connects the top portion of the reactor 12 to conduit 20. A control valve 30 is included in conduit 28. A compressor 32 is included in conduit 20. Compressor 32 compresses and transfers gas emanating from the reactor 12 or the receiving vessel 14 into the return tank 22.

Reactor 12 includes a sealable opening or access port (not shown) that permits material to be charged into the reactor 12. Reactor 12 also includes a mechanical stirring device 34 for mechanically agitating and stirring the contents of reactor 12 so as to form a homogeneous mixture. Preferably, the access port is equipped with a quick-opening, breech-lock system that requires no hand tools to open and close. Also, reactor 12 preferably includes a feed port having a valve (not shown) that facilitates the quick addition of minor amounts of material (e.g., polymer) to the reactor 12 once it has been pressurized.

Reactor 12 and receiving vessel 14 preferably are made of stainless steel. However, it will be appreciated that a number of alternative materials may be utilized, such as, for example, nickel-coated carbon steel or carbon steel vessels having chemically inert inserts or liners. A particularly desirable reactor 12 is shown in U.S. Pat. No. 6,054,103, referred to previously.

The length of conduit 13 is minimized as much as possible. Conduit 13 can be in the form of a constant-diameter tubing. Alternatively, an orifice can be disposed in the conduit 13 just prior to receiving vessel 14. In another alternative, a header 36 can be disposed in conduit 13 just prior to receiving vessel 14. The header 36 includes a nozzle having multiple openings through which the homogeneous mixture is sprayed. Any number of nozzle openings may be employed to spray the slurry. Of course, it will be appreciated that the selection of the proper nozzle will be a function of various parameters, such as, for example, the pressure employed in reactor 12, the size of particles and flow rates desired, and the starting materials and process medium being used.

Typically, an orifice in the conduit 13 or the openings in a spray nozzle in the header 36 have a diameter of from about 0.001 inch to about 1 inch, preferably from about 0.005 inch to about 0.5 inch, and more preferably from about 0.01 inch to about 0.1 inch. Examples of suitable spray nozzles are hydraulic atomizing nozzles sold by Spraying Systems Co. of Wheaton, Ill. Reference is made to application Ser. No. 09/315,616, referred to previously, for a disclosure of a particularly desirable control valve 26 and header 36.

Mechanical stirring device 34 comprises an electric motor 38 that drives a mixer 40. Mixer 40 may comprise any number of conventional mixing devices. The selection of the proper mixer will be a function of various parameters, such as, for example, the size of motor 38, the materials being mixed, the configuration of the reactor 12, the process medium being utilized and the pressure employed in vessel 12. An example of a suitable mixer 40 is a Cowles blade mixer sold by Indco, Inc. of New Albany, Ind. Reference is made to U.S. Pat. No. 6,054,103, referred to previously, for a disclosure of a particularly effective mixer 40. It will be appreciated that the present invention preferably provides for both distributive and dispersive mixing.

Apparatus 10 is employed in accordance with the present invention by first charging the starting materials for the orthopedic part that one desires to produce into the reactor 12. Reactor 12 then is sealed and isolated. The process medium from source 16 then is fed into reactor 12 via conduit 15 until a suitable quantity has been introduced into reactor 12. A critical temperature can be attained by heating reactor 12, heating the liquid/gas stream as it enters reactor 12, by agitating reactor 12, or by combinations of these techniques. The pressure and temperature in reactor 12 converts the process medium into a supercritical fluid.

Reactor 12 is maintained at an internal temperature of about −85° C. to about 200° C. When utilizing $CO_2$ as a process medium, a temperature of about 15° C. to about 160° C. is employed, and preferably about 20° C. to about 150° C., and more preferably about 31° C. to about 100° C. The particular temperature utilized will be a function of various variables such as, for example, the gas utilized, the composition of the starting materials, the pressures employed and equipment configurations. Pressure from about 350 psi to about 20,000 psi may be utilized. When employing a gas such as $CO_2$, a pressure of about 550 psi to about 7000 psi is utilized, and preferably about 950 psi to about 5000 psi, and more preferably about 1080 psi to about 4500 psi. The particular pressure utilized will be a function of such variables as the temperature of the reactor 12 and the particular process medium utilized.

Once reactor 12 has been heated and pressurized, motor 38 is energized and the starting materials and the supercritical fluid are thoroughly mixed to form a homogeneous, gas-saturated suspension, otherwise referred to as a supercritical fluid slurry. Preferably, reactor 12 is held below the melting point of the materials being processed. The temperature in reactor 12 preferably is in the range of from about 5 degrees below the $T_g$ (i.e., glass transition temperature) of at least one of the materials being processed up to about the melting point of such one material. In the case of an amorphous material, "melting point" means the temperature at which the material become wholly fluid. It is believed that a supercritical fluid will suppress the $T_g$ of most materials. In order to attain the desired temperature in reactor 12, reactor 12 may be equipped with heat exchangers or other suitable heating/cooling means.

The starting materials are mixed in reactor 12 for a period of about 1 to about 480 minutes, preferably about 5 to about 300 minutes and more preferably from about 30 to about 240 minutes. The viscosity of the supercritical fluid slurry is a function of the temperature and the density of the process medium. Once the starting materials have been thoroughly mixed, valve 26 is opened rapidly to minimize the pressure drop at valve 26. The pressurized supercritical fluid pushes the slurry out of the reactor 12. Valve 26 is maintained in the open position until such time as receiving vessel 14 (which is maintained at a lower pressure than reactor 12) has been filled and reactor 12 has been emptied of its contents. It has been found that best results are obtained if the flow within conduit 13 upstream of the header 36 is entirely laminar. Once receiving vessel 14 has been filled and substantially all of the starting materials have been transferred, valve 30 is opened in order to depressurize reactor 12 and permit the flow of gaseous process medium into return tank 22. The recycled process medium is made available for purposes of reuse by being transferred via conduit 24 to conduit 15.

While the slurry is being transferred to receiving vessel 14, receiving vessel 14 is held at a constant pressure. Preferably the pressure in receiving vessel 14 is lower than that in the reactor 12 so that the slurry enters receiving vessel 14 at a very high rate. Receiving vessel 14 is maintained at a starting temperature of about −85° C. to about 220° C., preferably about −18° C. to about 160° C., and more preferably about 0° C. to about 130° C. As with reactor 12, in order to maintain the desired temperature in receiving vessel 14, heat exchangers or other cooling/heating devices may be necessary. Preferably, receiving vessel 14 is maintained at a temperature below the melting point of the materials being processed. Receiving vessel 14 is maintained at a pressure of about 0 psi to about 5000 psi, preferably about 100 psi to about 2000 psi, and more preferably about 150 psi to about 1000 psi. The particular pressure and temperature utilized in receiving vessel 14 are a function of various variables, such as the particular process medium utilized and the composition of the starting materials.

The present invention uses a process medium that is capable of achieving a supercritical state. As used herein, the phrase "supercritical fluid" means a material that at specific temperatures and pressures no longer displays the properties of either a gas or a liquid. Examples of potential supercritical fluids suitable for use with the present invention include carbon dioxide, water, nitrous oxide, methane, ethane, ethylene, propane, pentane, benzene, methanol ethanol, isopropanol, various fluorocarbons such as cholrotrifluoromethane and monofluoromethane, toluene, pyridine, cyclohexane, decalin, cyclohexanol, o-xylene, and tetralin. The critical properties for these compounds are set forth below. The present invention contemplates the use of these compounds either by themselves or in combination. Additionally, it will be appreciated that solvents such as acetone, ketones, or ethers may be utilized in conjunction with the compounds listed below. Generally, however, the use of such solvents is not desired.

| Compound | Critical Temperature (° C.) | Critical Pressure (atm) |
| --- | --- | --- |
| $CO_2$ | 31.3 | 72.9 |
| $H_2O$ | 374.15 | 218.3 |
| $N_2O$ | 36.5 | 71.7 |
| Methane | −82.1 | 45.8 |
| Ethane | 32.28 | 48.1 |
| Ethylene | 9.21 | 49.7 |
| Propane | 96.67 | 41.9 |
| Pentane | 196.6 | 33.3 |
| Benzene | 288.9 | 48.8 |
| Methanol | 240.5 | 78.9 |
| Ethanol | 243.0 | 63.0 |
| Isopropanol | 235.3 | 47.0 |
| Isobutanol | 275.0 | 42.4 |
| Chlorotrifluoromethane | 28.0 | 38.7 |
| Monofluoromethane | 44.6 | 58.0 |
| Toluene | 320.0 | 40.6 |
| Pyridine | 347.0 | 55.6 |
| Cyclohexane | 280.0 | 40.2 |
| Decalin | 391.0 | 25.8 |
| Cyclohexanol | 356.0 | 38.0 |
| o-Xylene | 357.0 | 35.0 |
| Tetralin | 446.0 | 34.7 |

One compound that is particularly well suited for use with the present invention is carbon dioxide ($CO_2$). Carbon dioxide is preferred because it is nonflammable, reasonably priced, and is easily separated or removed from the constituents used in making orthopedic parts at the contemplated temperatures and pressures. Therefore, there will be no residual $CO_2$ in the finished products that could contribute to problems in use. The particular process medium employed to produce a particular orthopedic mixture can vary depending on such factors as the availability and cost of the medium, safety concerns, and working pressures and temperatures.

Although different process media may be used to produce the orthopedic mixtures in accordance with the principles of the present invention, care must be taken not to utilize starting materials that are soluble in the process medium at operating temperatures and pressures. If the starting materials are soluble in the process medium, it will not be possible to transfer the starting materials to the receiving vessel 14 without losing some of the starting materials to the storage tank 22, which would be a very undesirable result.

Starting materials that are used in the present invention are a source of calcium ions and a matrix for the calcium source. Optionally, additives such as growth factors or nutrients can be used. Because the orthopedic mixtures produced by the present invention are used in the human body, potentially harmful additives such as pigments, flow control agents, extenders, and the like should not be used.

Suitable sources of calcium ions include calcium phosphate ($Ca_3(PO_4)_2$), calcium hydroxy apatite ($3Ca_3(PO_4)2*Ca(OH)_2$), tri-basic calcium phosphate ($Ca_{10}(OH)_2(PO_4)_6$), durapatite ($3Ca_3(PO_4)2*Ca(OH)_2$), calcium salts of condensed phosphates, calcium sulfate ($CaSO_4$), gypsum hemi-hydrate and gypsum dihydrate. Salts of calcium acetate and other organic calcium salts also can be used, including monovalent, divalent, and multivalent complexes. Chelated complexes of calcium such as calcium edetate (EDTA) or other chelates of calcium may be used.

The matrix for the source of calcium ions is provided by a polymer, either thermoplastic, thermoset, or a combination of both. Polymers suitable for use in controlled drug release are discussed in K. Ulrich, et al., Polymeric Systems for Controlled Drug Release, Journal of the American Chemical Society (1999)("the Polymer Article"). It is believed that such polymers are suitable for use with the present invention. As noted in the Polymer Article, categories of suitable polymers include polyesters, polyorthoesters, polyanhydrides, polyamides, and phosphorous-containing polymers. It has been found that hydroxy-methyl cellulose and derivative-type polymers (e.g., hydroxy propyl cellulose) and polylactide-co-glycolide (e.g., Medisorb 8515 DL High I.V.) function well as part of the present invention. Other suitable polymers as specified in the Polymer Article include polyethylene, polypropylene, polyvinyl chloride, polyvinyl alcohol, polyethylene-vinyl acetate, polyenolketone, polyacrylic acid, polycarbophil, polyacrylamides, poly-N-isopropyl acrylamide, polyacrylates, polyethylene glycol, polyglycolic acid, polylactic acid, poly-ε-caprolactone, poly-3-hydroxybutyrate, polyortho esters, polyanhydrides, polyamino acids, pseudo-polyamino acids, polyamide-enamines, polyamido amines, polyurethanes, azopolymers, polydimethylsiloxane, and polyphosphazenes.

In those cases where the apparatus is used to make a bone filler, the starting materials should include an ultraviolet light-curable catalyst, or photoinitiator. Suitable catalysts are TPO (2,4,6-trimethyl benzoyl diphenyl phosphine oxide) commercially available from BASF, and DAROCUR 4265 and IRGACURE 261, both of which are commercially available from Ciba Specialty Chemicals. DAROCUR 4265 is a 50–50 mixture of HMPP (2-hydroxy-2-methyl-1-phenyl-propan-1-one) and TPO. IRGACURE 261 is $\eta^5$-2, 4-cyclopentadien-1-yl)[(1,2,3,4,5,6-η)-(1-methyl ethyl) benzene]-iron(+)-hexafluorophosphate(−1). These catalysts enable the finished mixture to be cured in situ and at a low temperature on the order of body temperature. Curing times are approximately 0.5–5.0 minutes, depending on the thickness of the filler.

When $CO_2$ gas is utilized as a process medium, $CO_2$ is charged to or utilized in reactor 12 so as to provide from about 10% by weight to about 90% by weight $CO_2$ and from about 90% by weight to about 10% by weight starting materials, preferably from about 20% by weight to about 80% by weight $CO_2$ and from about 80% by weight to about 20% by weight starting materials, and more preferably from about 40% by weight to about 60% by weight $CO_2$ and from about 60% by weight to about 40% by weight starting materials. After processing, the materials in receiving vessel 14 are a collection of homogeneous, uniformly sized particles. In the unlikely event that any oversize particles or an agglomeration of particles (foam) are contained in receiving vessel 14, the product must be rejected.

The amount of carbon dioxide absorbed and hence the amount of polymer swelling is proportional to temperature and pressure. For an amorphous polymer system the swelling could be as much as 66% or greater. This swelling leaves a large void volume within the polymer. As the polymer is reduced to ambient conditions, the rate of degassing or depressurization can influence the pore size of a subsequently produced orthopedic part and the interconnectivity of the void volumes therein. The depressurization is accomplished by way of controlled release from the receiving vessel 14 and a variable rate can be set. The density of the swollen polymer usually is equalized to that of the supercritical fluid density of the process medium. This permits the starting materials to be suspended in a mixture of equivalent density.

Although the apparatus 10 has been described as including various components downstream of the reactor 12 such as the conduit 13, receiving vessel 14, flush valve 26, etc., it is possible to produce acceptable product according to the invention without any such components. Suitable product can be prepared merely by mixing the supercritical fluid slurry in the reactor 12 and then releasing the internal pressure in a controlled manner. However, use of the components downstream of the reactor 12, particularly orifices or nozzles in the conduit 13, enables accurate control of particle size to be attained more easily. Because the particle size can be controlled accurately, bone implants or bone filler having predictable, desired characteristics can be produced easily.

The following Examples describe a method of producing an orthopedic mixture within the scope of the present invention. The apparatus used in the following Examples employed the a reactor 12, but did not include downstream components such as the flush valve 26, conduit 13, or receiving vessel 14. Unless otherwise indicated, all parts and percentages are by weight and all temperatures are in degrees Centigrade (° C.).

EXAMPLE 1

Three hundred sixty (360) grams of tri-basic calcium phosphate (TCP) ($Ca_3(PO_4)_2$) and 90 grams of PMMA resin (PD 7610) were charged into a one-gallon reactor 12. Reactor 12 was filled with 5.0 pounds of liquid $CO_2$ from source 16. The source 16 of $CO_2$ is a standard commercial source maintained at a temperature of about −18° C. and a pressure of about 300 psi. The filled reactor 12 was heated to 38° C. at a pressure of 1500 psi, thereby rendering the $CO_2$ a supercritical fluid. The starting materials and supercritical fluid were maintained under these conditions while being mixed for one hour using agitation device 34. The mixer 40 was rotated at a rate of 150 rpm. After one hour, the temperature was increased to 75° C., which caused the pressure to increase to 2900 psi. Mixing was continued for an additional 10 minutes at Upon completion of mixing as described, the $CO_2$ was released from reactor 12 until ambient pressure was attained. The reactor 12 was opened to yield a finely divided product containing 80% calcium phosphate.

The experiment was repeated with a 50:50 ratio of calcium to polymer and with different polymers (McWhorter 30–3011 and P-313). Suitable material ranges for the calcium phosphate starting material are 1–99% and 1–99% for the PCL polymer starting material. The pressure in the reactor 12 can be varied between 290–14,500 psi, the temperature can vary between 0–127° C., and the mixing rate can vary between 1–150 rpm.

EXAMPLE 2

Two hundred fifty (250) grams of a 50:50 mixture of hydroxyapatite (HA) ($HOCa_5(PO_4)_3$) and poly-e-caprolactone (PCL) was loaded into a one-gallon reactor 12. Reactor 12 was filled with 5.5 pounds of liquid $CO_2$ from source 16. The filled reactor 12 was heated to 38° C. and a pressure of 1600 psi, thereby rendering the $CO_2$ a supercritical fluid. The starting materials and supercritical fluid were maintained under these conditions while being mixed for one hour using agitation device 34. The mixer 40 was rotated at a rate of 145 rpm. After one hour, the temperature was increased to 65° C. and the pressure was increased to 3000 psi. Mixing was continued as 142 rpm.

Upon completion of mixing as described, water was turned on to cool the system as $CO_2$ was released from the reactor 12 until ambient pressure was attained. The reactor 12 was opened to yield a foamy product containing 50% HA.

The experiment was repeated many times. Other biodegradable polymers and various HA-to polymer ratios were employed. For example, 60% HA was used with 40% polylactic acid (L206) in one experiment, and 60% HA was used with 40% polylactide-co-glycolide (PLGA) (RG 752) in another. Forty percent (40%) HA was used with 60% PLGA and 30% HA was used with 70% PLGA (RG 755), both experiments being done at 160° C. Various ratios of HA to PCL also were tested successfully.

Suitable material ranges for the HA starting material are 1–99% and 1–99% for the PCL/PLGA polymer starting material. The pressure in the reactor 12 can be varied between 290–14,500 psi, the temperature can vary between 0–127° C., and the mixing rate can vary between 1–150 rpm.

EXAMPLE 3

A series of experiments were performed using various ratios of calcium sulfate ($CaSO_4$) and PCL. Calcium sulfate-PCL ratios varied between 80:20 and 60:40. All mixtures of calcium sulfate. and PCL were loaded into a one-gallon reactor 12. Reactor 12 was sealed, filled with liquid $CO_2$ from source 16, and heated to 38° C. at a pressure within the range of 2200–2400 psi, thereby rendering the $CO_2$ a supercritical fluid. The starting materials and supercritical fluid were maintained under these conditions while being mixed for one hour using agitation device 34. The mixer 40 was rotated at a rate of 150 rpm.

After one hour, the temperature was increased to 55° C. at a pressure within the range of 3100–3600 psi. Mixing was continued at 150 rpm. These conditions were maintained for an additional two hours. Thereafter, the pressure in the reactor 12 was reduced to ambient and porous products were recovered.

EXAMPLE 4

(Non-Experimental)

If it is desired to produce a bone filler, 0.25–3.0% of TPO can be added to the starting materials of Example 1. As in Example 1, a finely divided product will be produced. In order to cure the bone filler in situ, a monomer such as methyl methacrylate (MMA) can be added to the product to produce a paste of a desired viscosity. The paste can be applied to a fissure or other gap in a patient's bone. Thereafter, upon exposing the paste to ultraviolet light such as that produced by a medium mercury vapor pressure light, a free radical cure will be initiated. Cure time will be approximately 0.5–5.0 minutes, depending on the thickness of the paste.

EXAMPLE 5

(Non-Experimental)

If it is desired to use a cationic cure, a cationic photoinitiator such as IRGACURE 261 can be added to the starting materials of Example 1. In addition, a solid unsaturated monomer such as solid vinyl ether, which has a low melting temperature, can be added to the starting materials of Example 1. The resulting finely divided product will be cured upon exposure to ultraviolet light.

Although the invention has been described in its preferred form with a certain degree of particularity, it will be understood that the present disclosure of the preferred embodiment has been made only by way of example, and that various changes may be resorted to without departing from the true spirit and scope of the invention as hereinafter claimed. It is intended that the patent shall cover, by suitable expression in the appended claims, whatever features of patentable novelty exist in the invention disclosed.

What is claimed is:

1. A method for manufacturing an orthopedic mixture suitable for use as a bone substitute or bone filler, comprising:

providing a reactor having a mixer;

charging the reactor with starting materials that include a source of calcium ions, a matrix for the calcium ions, and a photoinitiator, the source of calcium ions being selected from the group consisting of calcium hydroxy apatite, tri-basic calcium phosphate, calcium salts of condensed phosphates, calcium sulfate, gypsum hemihydrate, gypsum dihydrate, monovalent, divalent, and multivalent complexes of salts of calcium acetate and other organic calcium salts, calcium edetate and other chelated complexes of calcium, and wherein the matrix for the calcium ions is a thermoplastic polymer, a thermoset polymer, or a combination of thermoplastic and thermoset polymers, the polymer being selected from the group consisting of hydroxy-methyl cellulose and its derivatives, polylactide-co-glycolide, polyethylene, polypropylene, polyvinyl chloride, polyvinyl alcohol, polyethylene-vinyl acetate, polyenolketone, polyacrylic acid, polycarbophil, polyacrylamides, poly-N-isopropyl acrylamide, polyacrylates, polyethylene glycol, polyglycolic acid, polylactic acid, poly-$\epsilon$-caprolactone, poly-3-hydroxybutyrate, polyortho esters, polyanhydrides, polyamino acids, pseudo-polyamino acids, polyamide-enamines, polyamido amines, polyurethanes, azopolymers, polydimethylsiloxane, and polyphosphazenes;

providing supercritical fluid in the reactor, the supercritical fluid being selected from the group consisting of carbon dioxide, water, nitrous oxide, methane, ethane, ethylene, propane, pentane, benzene, methanol ethanol, isopropanol, fluorocarbons, toluene, pyridine, cyclohexane, decalin, cyclohexanol, o-xylene, and tetralin;

the starting materials and the supercritical fluid being present in the reactor in proportions by weight ranging from 10:90 to 90:10 and more preferably 40:60 to 60:40;

mixing the starting materials and the supercritical fluid in the reactor for a period of time sufficient to form a supercritical fluid slurry;

reducing the pressure in the reactor to ambient; and recovering an orthopedic mixture from the reactor.

2. The method of claim 1, wherein the step of providing supercritical fluid in the reactor is accomplished by charging a liquid into the reactor, and thereafter heating and pressurizing the reactor contents so that the liquid attains a supercritical state.

3. The method of claim 2, wherein the liquid is carbon dioxide.

4. The method of claim 3, wherein the carbon dioxide is heated to a temperature within the range of 0–127° C. and is pressurized to a pressure within the range of 290–14,500 psi.

5. The method of claim 1, wherein, during the step of mixing, the reactor is maintained at a temperature below the melting point of the starting materials.

6. The method of claim 1, wherein the step of mixing is accomplished by a blade or helical mixer.

7. The method of claim 6, wherein the mixer is rotated at a speed within the range of 1–150 rpm.

8. The method of claim 1, wherein the photoinitiator is of the type that effects a free radical cure, and further comprising the steps of:

adding a monomer to the recovered orthopedic mixture; and exposing the monomer-containing orthopedic mixture to ultraviolet light.

9. The method of claim 8, wherein the photoinitiator is selected from the group consisting of TPO and HMPP, and the monomer is MMA.

10. The method of claim 1, wherein the photoinitiator is of the type that effects a cationic cure, and further comprising the steps of:

adding a solid monomer to the starting materials charged into the reactor; and exposing the monomer-containing orthopedic mixture to ultraviolet light.

11. The method of claim 10, wherein the photoinitiator is $\eta^5$-2,4-cyclopentadien-1-yl)[(1,2,3,4,5,6-$\eta$)-(1-methyl ethyl)benzene]-iron(+)-hexafluorophosphate(−1) and the monomer is MMA.

12. A method for manufacturing an orthopedic mixture suitable for use as a bone substitute or bone filler, comprising:

providing a reactor having a mixer;

providing a receiving vessel and a conduit that connects the reactor and the receiving vessel;

charging the reactor with starting materials that include a source of calcium ions, a matrix for the calcium ions, and a photoinitiator, the source of calcium ions being selected from the group consisting of calcium hydroxy apatite, tri-basic calcium phosphate, calcium salts of condensed phosphates, calcium sulfate, gypsum hemihydrate, gypsum dihydrate, monovalent, divalent, and multivalent complexes of salts of calcium acetate and other organic calcium salts, calcium edetate and other chelated complexes of calcium, and wherein the matrix for the calcium ions is a thermoplastic polymer, a thermoset polymer, or a combination of thermoplastic and thermoset polymers, the polymer being selected from the group consisting of hydroxy-methyl cellulose and its derivatives, polylactide-co-glycolide, polyethylene, polypropylene, polyvinyl chloride, polyvinyl alcohol, polyethylene-vinyl acetate, polyenol-ketone, polyacrylic acid, polycarbophil, polyacrylamides, poly-N-isopropyl acrylamide, polyacrylates, polyethylene glycol, polyglycolic acid, polylactic acid, poly-ε-caprolactone, poly-3-hydroxybutyrate, polyortho esters, polyanhydrides, polyamino acids, pseudo-polyamino acids, polyamide-enamines, polyamido amines, polyurethanes, azopolymers, polydimethylsiloxane, and polyphosphazenes;

providing supercritical fluid in the reactor, the supercritical fluid being selected from the group consisting of carbon dioxide, water, nitrous oxide, methane, ethane, ethylene, propane, pentane, benzene, methanol ethanol, isopropanol, fluorocarbons, toluene, pyridine, cyclohexane, decalin, cyclohexanol, o-xylene, and tetralin;

the starting materials and the superfluid materials being present in the reactor in proportions by weight ranging from 0:90 to 90:0 and more preferably 40:60 to 60:40 mixing the starting materials and the supercritical fluid in the reactor for a period of time sufficient to form a supercritical fluid slurry;

discharging the slurry into the receiving vessel through the conduit;

reducing the pressure in the receiving vessel to ambient; and recovering an orthopedic mixture from the receiving vessel.

13. The method of claim 12, wherein the step of providing supercritical fluid in the reactor is accomplished by charging a liquid into the reactor, and thereafter heating and pressurizing the reactor contents so that the liquid attains a supercritical state.

14. The method of claim 13, wherein the liquid is carbon dioxide.

15. The method of claim 14, wherein the carbon dioxide is heated to a temperature within the range of 0–127° C. and is pressurized to a pressure within the range of 290–14,500 psi.

16. The method of claim 12, wherein, during the step of mixing, the reactor is maintained at a temperature below the melting point of the starting materials.

17. The method of claim 12, further comprising the step of providing an orifice in the conduit.

18. The method of claim 17, wherein the orifice has a diameter within the range of about 0.01 inch to about 0.10 inch.

19. The method of claim 12, further comprising the step of providing a nozzle having multiple openings in the conduit.

20. The method of claim 14, wherein the openings in the nozzle have a diameter within the range of about 0.01 inch to about 0.10 inch.

21. The method of claim 12, wherein the step of mixing is accomplished by a blade or helical mixer.

22. The method of claim 21, wherein the mixer is rotated at a speed within the range of 1–150 rpm.

23. The method of claim 12, wherein the photoinitiator is of the type that effects a free radical cure, and further comprising the steps of:

adding a monomer to the recovered orthopedic mixture; and exposing the monomer-containing orthopedic mixture to ultraviolet light.

24. The method of claim 33, wherein the photoinitiator is selected from the group consisting of TPO and HMPP, and the monomer is MMA.

25. The method of claim 12, wherein the photoinitiator is of the type that effects a cationic cure, and further comprising the steps of:

adding a solid monomer to the starting materials charged into the reactor; and exposing the monomer-containing orthopedic mixture to ultraviolet light.

26. The method of claim 25, wherein the photoinitiator is $\eta^5$-2,4-cyclopentadien-1-yl)[(1,2,3,4,5,6-$\eta$)-(1-methyl ethyl)benzene]-iron(+)-hexafluorophosphate(-1) and the monomer is MMA.

27. An orthopedic mixture produced by the method of claim 1.

28. An orthopedic mixture produced by the method of claim 12.

29. An orthopedic mixture that, upon curing, simulates autogenic bone, comprising:

a monomer in the form of MMA;

a source of calcium ions, the calcium ions being selected from the group consisting of calcium hydroxyapatite, tri-basic calcium phosphate, calcium salts of condensed phosphates, calcium sulfate, gypsum hemi-hydrate, gypsum dihydrate, monovalent, divalent, and multivalent complexes of salts of calcium acetate and other organic calcium salts, calcium edetate and other chelated complexes of calcium;

an ultraviolet light-curable catalyst selected from the group consisting of TPO, HMPP, and $\eta$5-2,4-cyclopentadien-1-yl)[(1,2,3,4,5,6-$\eta$)-(1-methyl ethyl)benzene]-iron(+)-hexafluorophosphate(−1); and a polymer matrix in which the monomer, the source of calcium ions and the ultraviolet light-curable catalyst are suspended, the matrix being in the form of a thermoplastic polymer, a thermoset polymer, or a combination of thermoplastic and thermoset polymers, the polymer being selected from the group consisting of hydroxy-methyl cellulose and its derivatives, polylactide-co-glycolide, polyethylene, polypropylene, polyvinyl chloride, polyvinyl alcohol, polyethylene-vinyl acetate, polyenol-ketone, polyacrylic acid, polycarbophil, polyacrylamides, poly-N-isopropyl acrylamide, polyacrylates, polyethylene glycol, polygycoiic acid, polylactic acid, poly-ε-caprolactone, poly-3-hydroxybutyrate, polyortho esters, polyanhydiides, polyamino acids, pseudo-polyamino acids, polyamide-enamines, polyamido amines, polyurethanes, azopolymers, polydimethylsiloxane, and polyphosphazenes.

* * * * *